US009022653B2

(12) United States Patent
Pittet et al.

(10) Patent No.: US 9,022,653 B2
(45) Date of Patent: May 5, 2015

(54) FLEXIBLE MULTICHAMBER BAG

(75) Inventors: Michel Pittet, Aumont (CH); Caroline Ansermet, Denges (CH); Bastien Ecabert, Bussigny (CH); Cedric Berchier, La Tour-de-Peilz (CH)

(73) Assignee: B. Braun Melsungen AG, Melsungen (DE)

( * ) Notice: Subject to any disclaimer, the term of this patent is extended or adjusted under 35 U.S.C. 154(b) by 300 days.

(21) Appl. No.: 13/642,135

(22) PCT Filed: May 2, 2011

(86) PCT No.: PCT/EP2011/056962

§ 371 (c)(1), (2), (4) Date: Oct. 19, 2012

(87) PCT Pub. No.: WO2011/141318

PCT Pub. Date: Nov. 17, 2011

(65) Prior Publication Data

US 2013/0039606 A1 Feb. 14, 2013

(30) Foreign Application Priority Data

May 10, 2010 (EP) .................................... 10162376

(51) Int. Cl.

| | |
|---|---|
| ***B65D 33/22*** | (2006.01) |
| ***B65D 33/10*** | (2006.01) |
| ***B65D 33/00*** | (2006.01) |
| ***B65D 65/26*** | (2006.01) |
| ***B65D 33/16*** | (2006.01) |
| ***A61B 19/00*** | (2006.01) |
| ***A61J 1/10*** | (2006.01) |
| ***A61J 1/20*** | (2006.01) |

(52) U.S. Cl.

CPC *A61J 1/10* (2013.01); *A61J 1/2093* (2013.01); *A61J 2001/2024* (2013.01)

(58) Field of Classification Search

USPC ......................... 383/38, 210–211, 9, 67, 906; 604/406–410, 416

See application file for complete search history.

(56) References Cited

U.S. PATENT DOCUMENTS 6,231,559 B1 * 5/2001 Loretti .......................... 604/410
6,468,259 B1 * 10/2002 Loretti et al. ................ 604/410

(Continued)

FOREIGN PATENT DOCUMENTS

CN 101547673 A 9/2009
DE 9401288.1 U1 4/1994

(Continued)

*Primary Examiner* — Jes F Pascua

(74) *Attorney, Agent, or Firm* — Clements Bernard PLLC; Gregory N. Clements

(57) ABSTRACT

The present invention refers to a flexible multiple chamber bag comprising:

a) three adjacent chambers, a first chamber partially separating a second upper chamber from a third lower chamber by first and second welded seams,
b) said second chamber and said third chamber being partially connected by a third welded seam,
c) said first welded seam being non-peelable and said second and third welded seams being peelable said second and third welded seams having the shape of an inverse letter "V" each second and third welded seam starting at the basic point of said "V" and terminating essentially in a right angle at the circumference weld of said bag, said bag comprising a hanger flap extending from the top end of said bag and a medical port welded to the lower end of said circumferential weld.

5 Claims, 1 Drawing Sheet

(56) References Cited

U.S. PATENT DOCUMENTS

| | | | | |
|---|---|---|---|---|
| 7,770,611 | B2 * | 8/2010 | Houwaert et al. | 141/114 |
| 7,875,015 | B2 * | 1/2011 | Pahlberg et al. | 604/410 |
| 7,875,016 | B2 * | 1/2011 | Pahlberg et al. | 604/410 |
| 7,954,596 | B2 | 6/2011 | Schulze et al. | |
| 2004/0134802 | A1 * | 7/2004 | Inoue et al. | 206/219 |
| 2008/0004594 | A1 * | 1/2008 | Pahlberg et al. | 604/410 |
| 2009/0166363 | A1 | 7/2009 | Balteau | |
| 2009/0254032 | A1 | 10/2009 | Muramatsu | |
| 2010/0198185 | A1 * | 8/2010 | Gorisch | 604/410 |
| 2010/0318058 | A1 * | 12/2010 | Schroder | 604/410 |
| 2013/0046271 | A1 * | 2/2013 | Pittet et al. | 604/410 |

FOREIGN PATENT DOCUMENTS

| | | | |
|---|---|---|---|
| DE | 4410876 | A1 | 10/1995 |
| DE | 19605357 | A1 | 8/1997 |
| DE | 19811276 | C1 | 1/2000 |
| EP | 0295204 | B1 | 12/1988 |
| EP | 0790051 | B1 | 8/1997 |
| EP | 1773277 | B1 | 10/2008 |
| EP | 1011605 | B2 | 6/2009 |
| WO | 9737628 | A1 | 10/1997 |
| WO | 2007037793 | A1 | 4/2007 |
| WO | 2008069731 | A1 | 6/2008 |
| WO | WO 2008/069731 | A1 | 6/2008 |

* cited by examiner

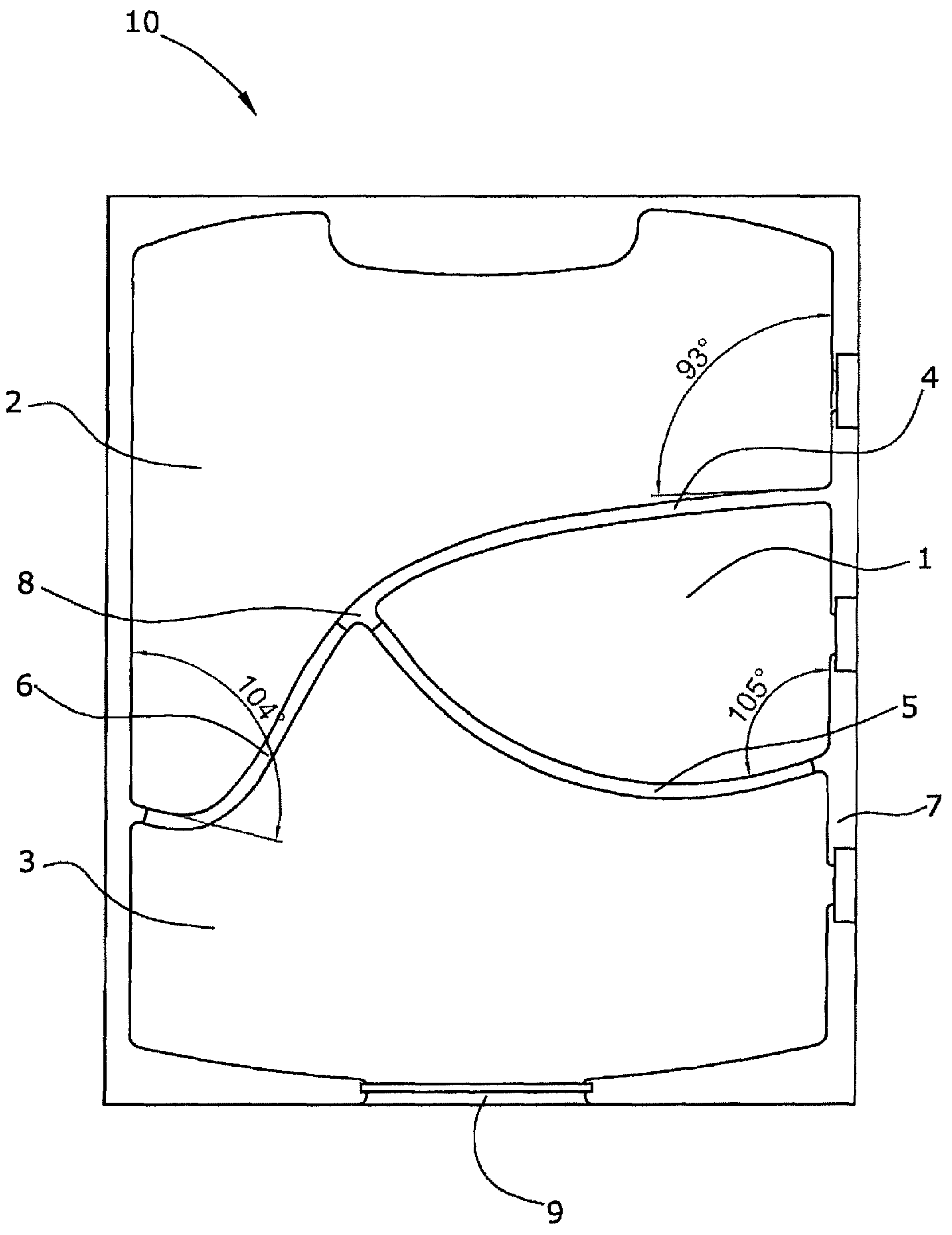
10
2
93°
4
1
8
6
104°
105°
5
7
3
9

FLEXIBLE MULTICHAMBER BAG

FIELD OF THE INVENTION

The present invention refers to a flexible multiple chamber bag for storing medical products comprising three chambers.

BACKGROUND

In the pharmaceutical industry and especially in the field of perfusion solutions, impermeable flexible bags are extensively used. Such bags or containers are prepared from polymerized materials which have to meet a wide variety requirements. Thus, in particular, gas and vapor tightness, transparency, printability and inertness towards the substances they contain, are of essential importance. The substances contained in the containers or bags essentially consist of salts and solutions thereof, carbohydrates, amino acids and lipids. They are usually employed in multicompartment bags, the individual compartments or chambers being filled with different components.

DE 44 10 876 A1 relates to a multicompartment bag made of a polymeric material, who's bag compartments are formed by welds in the peripheral (circumferential) region and by at least one weld in the intercompartment region, the welds being formed from the polymeric materials facing the compartments.

EP 0 295 204 B1 describes a container for medical use, in particular a container for infusions consisting of an envelope made of a flexible, homogeneous, polymerized material which is divided into three compartments, separated from each other by leaktight welds of the envelope material and each of said compartments is provided with an occluded passage which can be opened deliberately to enable the contents of the part of the interior space to flow into another one, wherein the container has two adjacent compartments (3,4) of the interior space within the upper portion thereof and one compartment (5) in its lower part within the lower portion thereof and is intended for taking up and mixing subsequently lipids, amino acids, and sugars just before the use thereof, wherein each compartment is provided with one occludable opening in order to supply the compound through said opening or to discharge the contents thereof through said opening outwards, and wherein the material of the envelope is chemically and biologically inert against any envisaged compound and the mixtures thereof.

DE 94 01 288 U1 pertains a multichamber bag having at least two chambers being arranged one upon another during the mixing stage and being surrounded by an exterior boundary, said chambers being separated from another by at least one bar and forming an upper chamber and a mixing chamber, said bag having at least one connecting device being arranged within the bar and being closed by a locking device which is to be opened, said connecting device providing a flow connection between the chambers after being opened, said bag having at least one hang up opening at the upper boundary region and a discharge device being arranged at the mixing chamber as well as a second discharge device being opposite to said former discharge device and being arranged in the circumferential region of the mixing chamber.

DE 196 05 357 A describes a flexible plastic container 1 for the spatially separated storage and, optionally selective sterilization of the ingredients of preparations for parenteral or enteral use, comprising at least four compartments, 2,3,4, and 5, and, optionally, a compartment 6 being suited for taking up trace elements within compartment 2, carbohydrates within compartment 3, fats within compartment 4, and amino acid solutions within compartment 5, and, optionally, electrolytes and/or vitamins within compartment 6, said container having one of the closable fill in openings 7, 8, 9 and 10, and, optionally, 11, each; one discharge opening 12 for administering the mixture of ingredients of the preparations for parenteral or enteral use; connecting means 13, 13', 14,14' and 15, 15' and, optionally, 16, 16' which can be opened sterilely from the outside, by which flow connections between the compartments 2,3,4 and 5 and, optionally 6, respectively, can be provided; wherein the proportions by volume of compartments 2,3,4 and 5 and, optionally 6 are selected such that in the working position as resulting from suspending by hang up means 17 a complete mixture of all ingredients within compartment 5 is possible by opening the connecting means 13,13', 14, 14' and 15, 15', and optionally 16, 16'; the proportion by volume of compartment 2 to compartment 3 is selected such that in the working position as resulting from suspending by hang up means 17 a complete mixture of the ingredients of compartments 2 and 3 within compartment 3 is possible by opening the connecting means 13, and, optionally, the proportion by volume of compartment 4 to compartment 6 is selected such that in the working position as resulting from suspending by hang up means 17 a complete mixture of the ingredients of compartments 4 and 6 within compartment 4 is possible by opening the connecting means 16, 16'.

EP 1 011 605 B2 relates to a flexible plastic container (1) for the spatially separated storage and, optionally, selective sterilization of the ingredients of preparations of parenteral or enteral use, consisting of only three compartments, a first compartment (3, a second compartment (4) and a third compartment (5), said compartments being separated from each other by means of Ieaktight welds of the envelope material, said compartments having one closable fill in opening (7), (8) and (9), each; connecting means (10) and (11) which are formed as peelable heat-sealed welds which can be opened sterilely from the outsides, by which respective flow connections between compartments (3), (4) and (5) are selected such that in the working position as resulting from suspending by the hang up means (12) a rapid and complete mixture of all ingredients within the third compartment (5) is possible by opening the connecting means (10) and (11), characterized in that the first compartment (3) contains carbohydrates, the second compartment (4) lipid and the third compartment (5) amino acids.

WO 2007/037793 A1 relates to a multiple chamber container for separately storing components of a parenteral nutritional formulation. The multiple chamber container may include frangible barriers, preferably peelable seals separating the chambers from each other. The container preferably facilitates the selective activation of the peelable seals to permit the admixing of less than all the separately stored components. The container may include a chamber positioned at each other of the opposite lateral ends of the container and at least one additional chamber between the lateral chambers. The at least one additional chamber may have a longitudinal length substantially less than the longitudinal length of at least one of the lateral chambers. This configuration allows for selective opening of the seals since when rolling the container from the top avoids pressurizing the at least one additional chamber and inadvertent activation of a seal. The longitudinal length of the at least one additional chamber may be from about two-thirds to about three-fourths the longitudinal length of at least one of the lateral chambers. Alternatively, the container may include a hanger flap extending from a top end of the container towards the bottom end of substantially greater distance relative to the at least one additional chamber than the lateral chambers.

EP 1 773 277 B1 relates to a container for storage a pharmaceutical agent made of a flexible polymeric film wherein the container comprises at least one peelable seal comprising at least two substantially straight sections (7,8), which are connected by a curved rupture zone (5), the curved rupture zone (5) of the peelable seal being formed as an arc of a circle having a central angle of at least 60° and being curved over its whole length between the straight sections (7,8), characterized in that the curved rupture zone (5) is formed as an arc of a circle with a radius of 5 to 75 mm, wherein the radius is measured from the central point of the circle to a point of the outer edge of the seal, wherein the outer edge is the edge that is more dislodged from the central point than the inner edge, and that the substantially straight sections (7,8) of the peelable seal form an angle of 150 ° to 180°.

WO 97/37628 relates to an improved container for parenteral fluids. Said publication in particular discloses a flexible transparent container for improved storage of oxygen sensitive parenterally administrable agents comprising an inner, primary container enclosed in a substantially oxygen impermeable outer envelope with an oxygen absorber, capable of consuming essentially all residual oxygen after the outer envelope is sealed, and for sufficient period also the oxygen penetrating said envelope. The inner container is made of a polypropylene containing flexible polymeric material compatible with lipophilic agents capable of forming both permanent and peelable seals, while the envelope is made of a substantially water impermeable flexible multilayered polymeric material comprising a first outer substantially water impermeable polymeric film with oxygen barrier forming capacity, assembled with a second, inner polymeric film with a supplementary oxygen barrier forming capacity. The container essentially maintains its characteristics after being subjected to sterilization by steam or radiation.

The peelable seams 50 and 50' according to FIG. 1 have the shape of an inverse letter "V" with an increasing angle of the lines of said "V" from the basic point of said "V". The inner container shown in FIG. 1 is a bag formed and provided with three parallel chambers 31,32,33 which may have the same or different volumes dependent on the desired amount the stored product. The two seams 50,50' separating the chambers are typically formed by peelable seal weldings in the container which are highly tight, but possible rupture by a predetermined motion of the user. It is preferred herein to fill in the carbohydrates solution in the top chamber 31, whereas the middle chamber 32 contains the lipid emulsion while accordingly, the amino acid solution is designated to be filled in the lower chamber 33. Nevertheless, said construction cannot ensure even in case of an abuse of the nurse, that in a first instance the incompatible lipid emulsion and the carbohydrate solution is mixed prior to the admixture of the amino acid. Furthermore, the rectangular termination of the welding seams 50,50' to the circumferential weld may result in a dead volume in the corners of said connection.

The core of this patent is a curved rupture zone 5 being formed as an arc of a circle with a defined radius. However, since the peelable seals 41, 32 and 33 extend to the lower weld 25, there always exist a dead volume and thus, the content of the container cannot be used for complete administration to the patient. Similarly, the rupture zone 39 in FIG. 3 of EP 1 773 277 B1 does not ensure a complete usage of the material contained in the bag.

Thus, it is the aim the present invention to simplify the final structure of a flexible multiple chamber bag 10 for storing medical products and to improve the use thereof by the nurse. Furthermore, it should be ensured, that the ingredients, namely fat and amino acids are first mixed before adding the glucose or carbohydrate. Thus, the object of the invention in particular is to avoid a first mixture of glucose and fat independent from any potential abuse of the bag by the nurse.

SUMMARY OF THE INVENTION

The above objects of the invention are met in a first embodiment of the invention by a flexible multiple chamber bag 10 for storing medical products comprising:

a) three adjacent chambers, a first chamber 1 partially separating a second upper chamber 2 from a third lower chamber 3 by first and second welded seams 4 and 5, b) said second chamber 2 and said third chamber 3 being partially connected by a third welded seam 6, c) said second and third welded seams 5 and 6 being peelable when applying pressure on the bag 10, said second and third welded seams 5 and 6 having the shape of an inverse letter "V" with increasing angle of the lines of said "V", each second and third welded seam 5 and 6 starting at the basic point 8 being in connection with chambers (1,2,3), said second and third welded seams (5) and (6) of said "V" terminating essentially in a right angle to the circumference weld 7 of said bag 10, d) said basic point 8 of said "V" being fixed and non peelable when applying pressure on the bag 10, e) said first welded seam 4 being non peelable when applying pressure on the bag 10, starting at the basic point 8 of said "V" and terminating essentially in a right angle at the circumference weld 7 of said bag 10, f) said bag 10 comprising a hanger flap extending from the top end of said bag 10 next to said chamber 2 within said circumferential weld 7 and g) a medical port 9 welded to the lower end of said circumferential weld 7.

BRIEF DESCRIPTION OF THE DRAWING

The FIGURE is a side view of a multichamber bag.

DETAILED DESCRIPTION OF THE INVENTION

Due to the specific geometry of the separation of the three chambers, the object of the invention as outlined above is met.

The FIGURE in detail shows a flexible multiple chamber bag 10 according to the present invention, which is intended for storing medical products therein.

The multiple chamber bag according to the present invention in FIG. 1 contains three adjacent chambers 1,2,3 although additional chambers may be added without disturbing the geometry of the first, second and third welded seams 4, 5 and 6.

An upper chamber 2 and a lower chamber 3 are separated by first and third welded seam 4, 6 which as such extend from the right to the left circumferential weld of the multiple chamber bag. However, said first and third weld seams 4,6 although terminating essentially in a right angle to the circumferential weld 7 does not extend as a linear weld, it contains a non-peelable part 4 and a peelable part 6 which together form a wing.

However, in order to ensure the complete emptying of the material being contained therein, the connection of the welds 4 and 6 to the circumferential weld 7 terminate in an angle of more 90° to 105°, relative to the top and of said bag 10. Such an angle avoids any dead volume in such a corner and allows the complete use of the content of the multiple chamber bag. The same consideration of course applies to the peelable second weld 5.

The second and third seams 5 and 6 are peelable when applying pressure on the bag 10 independent from the technique of the nurse applying said pressure by rolling the multiple chamber bag or by applying pressure by hand.

In accordance with the claim language concerning the geometry of the first and second welded seams 4 and 5 also enclosed herewith is form of a lying letter "U" extending from the circumferential weld 7 being connected with the upper ends of the letter "U" and the lowest part of the letter "U" being part of the basic point 8. Third welded seam 6 may be outlined as a relative straight line between the basic point 8 and the circumferential weld 7. Again second welded seam 5 is peelable, whereas first welded seam 4 remains as it is even when applying pressure to the bag. Again, this configuration allows a practically total emptying of bag in use.

In an preferred embodiment, the multichamber bag according to the present invention is made of a flexible polymeric film having a region with a higher melting point designated as its outside and having a region with a lower melting point designated as its sealing inside, which can be sealed together by means of conventional welding tools to permanent or peelable seams. It is to be understood that the inner region is intended to face the stored components and can form both, permanent seams and different peelable seams when subjected to different welding conditions or operations. It is in particular preferred that the film is made of at least two different polymer layers wherein the inside layer is a sealant layer being capable of forming both, permanent seams and peelable seams when subjected to welding at different temperatures. Polymeric material providing said features are known from the prior art as defined above.

There is always a balance between the demands to have a peelable seam being strong enough to withstand the manufacturing process of the multichamber bag and on the other hand to be easy to open for the nurse. Flexible multichamber bags with peelable seams of low seal strength for example 5 to 10 N/30 mm can be readily opened but seams of low strength can be damaged during manufacturing or transport of the multichamber bag. For this reason, it is advantageous in accordance with the prior art to manufacture peelable seams with a seal strength of at least 30 N/30 mm and more preferably with a seal strength of 40 N/30 mm.

The extension of said second and third welded seams 5 and 6 has the shape of an inverse letter "V" with increasing angle of the lines of said "V" from the basic point 8 of said "V". Preferably the angle of the letter "V" is increased continuously avoiding hard corners to be peeled. An appropriate "V" without said increasing angle would result in a termination of said second and third welds 5,6 in an angle at the circumferential weld 7 of said bag of less than 90° relative to the top and of said bag 10 and thus would result in a dead volume. Thus, the wing-like appearance of the peelable second and third seams 5 and 6 ensures the option of a complete emptying of the flexible multiple chamber bag.

The basic point 8 of said "V" may be fixed due to the extension of the non-peelable seal 4 even when applying pressure on the bag 10 as being part of the non-peelable first seam 4. In an alternative embodiment the basic point 8 may be part of the peelable second and third seams 5 and 6 and thus, opens when applying pressure on the bag 10. In this case a continuous second and third weld 5 and 6 opens. Thus, the exact position thereof is determined by the appearance of the first, second and third seams 4,5,6. Even in case the nurse puts pressure on the wrong part of the multichamber bag, its construction in any case prohibits a first incompatible mix of lipids and glucose (carbohydrate) and furthermore an administration of a high concentrated glucose solution without the admixture of the amino acids and the lipid to the patient.

A bag 10 according to the present invention comprises a hanger flap extending from the top and of said bag next to the chamber 2 in particular within the circumferential weld 7.

In a preferred embodiment the multichamber bag 10 according to the present invention does no longer contain any ports for the introduction of the contents to chambers 1,2,3 but only contains a medical port 9 welded to the lower and of said circumferential weld 7.

As mentioned above, the bag 10 according to the present invention in particular contains medical products, such as solutions, emulsions, suspensions and/or dispersions suitable for parenteral or enteral nutrition of patients.

In particular, chamber 1 partially separating chamber 2 and chamber 3 contains a fat emulsion. Accordingly, the upper chamber 2 contains a carbohydrate solution and the lower chamber 3 contains an amino acid solution. The features of the bag as described above ensure a rapid mixing and complete emulsification of all contents of the container.

A second embodiment of the present invention relates to the use of a bag as described above for the selective sterilisation, spatially separate storage, rapid mixing and administration of carbohydrates, lipids and amino acids.

The invention claimed is:

1. A flexible multiple chamber bag (10) for storing medical products comprising:

a) three adjacent chambers, a first chamber (1) partially separating a second upper chamber (2) from a third lower chamber (3) by first and second welded seams (4) and (5), said bag having a circumference weld (7) around its circumference, wherein a portion of said first chamber (1), said second upper chamber (2) and said third lower chamber (3) are bound by said circumference weld (7), b) said second chamber (2) and said third chamber (3) being partially connected by a third welded seam (6), said first, second, and third welded seams (4), (5) and (6) intersect creating basic point (8), c) said second and third welded seams (5) and (6) being peelable when applying pressure on the bag (10), said second and third welded seams (5) and (6) having the shape of an inverse letter "V" with continuously increasing angle of the lines of said "V", each second and third welded seam (5) and (6) starting at the basic point (8) being in connection with chambers (1,2,3), said second and third welded seams (5) and (6) of said "V" terminating essentially in a right angle to the circumference weld (7) of said bag (10), d) said basic point (8) of said "V" being fixed and non peelable when applying pressure on the bag (10), e) said first welded seam (4) being non peelable when applying pressure on the bag (10), starting at the basic point (8) of said "V" and terminating essentially in a right angle at the circumference weld (7) of said bag (10), said non-peelable first welded seam (4) together with said peelable third welded seam (6) form a wing, f) said bag (10) comprising a hanger flap extending from the top end of said bag (10) next to said chamber (2) within said circumferential weld (7) and g) a medical port (9) welded to the lower end of said circumferential weld (7).

2. The bag (10) according to claim 1, characterized in that said medical products encompass solutions, emulsions, suspensions and/or dispersions suitable for parenteral or enteral nutrition of patients are contained within said bag.

3. The bag (10) according to claim 1, characterized in that chamber (1) contains a fat emulsion, chamber (2) contains a carbohydrate solution and chamber (3) contains an amino acid solution.

4. The bag (10) according to claim 1, characterized in that said first second, and third welds (4), (5) and (6) each terminate at the circumferential weld (7) in an angle of more than 90° to 105° , relative to the top end of said bag (10).

5. The use of a bag (1) according to claim 1 for the selective sterilisation, spatially separate storage, rapid mixing and administration of carbohydrates, lipids and amino acids.

* * * * *